(12) United States Patent
Boer

(10) Patent No.: US 6,630,596 B2
(45) Date of Patent: Oct. 7, 2003

(54) COMPOSITION AND EMULSIFIER

(75) Inventor: Willem George Boer, Edenvale (ZA)

(73) Assignee: Chemical Services Limited (ZA)

( * ) Notice: Subject to any disclaimer, the term of this patent is extended or adjusted under 35 U.S.C. 154(b) by 0 days.

(21) Appl. No.: 10/087,468

(22) Filed: Mar. 1, 2002

(65) Prior Publication Data

US 2002/0182170 A1 Dec. 5, 2002

Related U.S. Application Data

(63) Continuation of application No. PCT/ZA00/00154, filed on Aug. 31, 2000.

(30) Foreign Application Priority Data

Sep. 2, 1999 (ZA) .............................. 99/5665

(51) Int. Cl.$^7$ ..................... C07D 307/66; C07D 307/70
(52) U.S. Cl. ................... 549/253; 549/321; 549/323
(58) Field of Search ................................. 549/253, 321, 549/323; 516/29, 72; 44/351

(56) References Cited

FOREIGN PATENT DOCUMENTS

EP           0 360 394 A3      3/1990    ........... C06B/47/14

OTHER PUBLICATIONS

Anonymous, "Dispersants for use in lubricating oils and fuels—comprise alkyl or aklenyl—substd. succinimide (s), obtd. from 3–25C polyamine and alk(en)yl–substd. succinic anhydride" (Abstract), *Derwent Publications Ltd., London; Database WPI acc No.: 1987–133766/198719 XRAM Acc No.: C87–055971—XP0021551615*, 2 pages (Apr. 10, 1987).

*Primary Examiner*—Taofiq Solola
(74) *Attorney, Agent, or Firm*—Schwegman, Lundberg, Woessner & Kluth, P.A.

(57) ABSTRACT

The invention relates to an adduct of polyalk(en)yl succinic anhydride and a compound of formula (I): wherein $R_1$ is hydrogen, hydroxyl, hydrocarbyl, hydroxyhydrocarbyl, carbamyl, 1-acetyl, amino, or nitro; $R_2$ is hydrogen, hydroxyl, hydrocarbyl, hydroxyhydrocarbyl, carbamyl, 1-acetyl, amino, or nitro; $R_3$ is hydrogen or hydrocarbyl; and X is O, S or NH; or a derivative of such an adduct. The invention also relates to an emulsifier comprising such an adduct or derivative, and the invention also relates to compositions including such an emulsifier.

22 Claims, No Drawings

COMPOSITION AND EMULSIFIER

CROSS-REFERENCE TO RELATED APPLICATIONS

This application is a continuation under 35 U.S.C. 111(a) of International Application No. PCT/ZA00/00154 filed Aug. 31, 2000 and published in English as WO 01/16056 A1 on Mar. 8, 2001, which claims priority from South African Application No. 99/5665 filed Sep. 2, 1999, which applications are incorporated herein by reference.

FIELD OF THE INVENTION

This invention relates to novel compounds or compositions and methods of preparing same. The invention also relates to emulsifiers, especially to emulsifiers for use in explosive compositions, especially emulsion explosive compositions. The invention further relates to explosive compositions especially emulsion explosive compositions.

DESCRIPTION OF RELATED ART

Emulsion explosives are in large scale commercial use around the world. They are made up of two inmiscible liquid phases in a stable emulsion. Usually such an emulsion comprises a discontinuous aqueous phase in a continuous lipid phase. The aqueous phase usually contains a high concentration of oxidiser salts such as ammonium, sodium or calcium nitrates. The lipid phase acts as a fuel and usually consists of selected petroleum products (oils). An emulsifier in the form of a surface-active chemical is required to form a stable, useful emulsion.

Emulsions are often made by mixing a hot concentrated solution of inorganic oxidiser salts in water, with a petroleum oil that has a suitable emulsifier dissolved in it. The resulting emulsions are technically unusual in that they are high internal-phase invert ("water-in-oil") emulsions, are very viscous, and the highly concentrated oxidiser salts in the disperse phase droplets should not crystallise out on cooling of the emulsion as one would expect. Durable, stable supersaturation occurs in these droplets. When crystallisation does occur, the explosive capability of the emulsion diminishes and is lost. This is a good fail-safe feature for old explosives but it is most undesirable in most commercial explosive products that need to be stored or kept for some period before actual use.

As is well known to those skilled in the art, a key to a good emulsion product is the emulsifier, which is a chemical whose molecules preferentially occupy the interface between the two phases thereby forming a barrier layer and preventing coalescence of the dispersed phase droplets. The emulsion is thus rendered stable.

During the 1970's/1980's the use of polyisobutenyl succinic anhydride ("PIBSA") derivatives as superior emulsifiers for emulsion explosives was commenced with. The main classes of organic chemicals that will form an adduct with PIBSA are alcohols, polyols, amines and alkanolamines. Since the 1980's emulsifiers in the form of the adduct of monoethanolamine or diethanolamine of PIBSA have been sold and exploited.

The inventor of the present invention has now prepared the adduct of PIBSA with urea. It was not expected that urea would react with PIBSA to form a material useful as an emulsifier in the preparation of emulsion explosives. Surprisingly it was found that this adduct showed superior performances as an emulsifier in emulsion explosives, compared to known products such as the adduct of monoethanolamine with PIBSA. A sample of an emulsion explosive composition containing the adduct of PIBSA and urea displayed a longer shelf life (slower crystallisation of oxidiser salts) than control samples made at the same time with the adduct of PIBSA and monoethanolamine. As far as the inventor is aware, last mentioned adduct has up to now given the best available shelf life.

It is accordingly one object of the present invention to provide an alternative emulsifier.

SUMMARY

According to one aspect of the present invention there is provided an adduct of polyalk(en)yl succinic anhydride and a compound of formula:

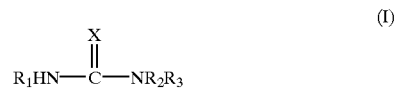
(I)

wherein
R$_1$ is hydrogen, hydroxyl, hydrocarbyl, hydroxyhydrocarbyl, carbamyl, 1-acetyl, amino, or nitro;
R$_2$ is hydrogen, hydroxyl, hydrocarbyl, hydroxyhydrocarbyl, carbamyl, 1-acetyl, amino, or nitro;
R$_3$ is hydrogen or hydrocarbyl; and
X is O, S or NH;
or a derivative of such an adduct.

When X is NH, then R$_1$ and R$_3$ are preferably hydrogen and R$_2$ is preferably hydrogen or nitro. Preferably the compound of formula (I) is guanidine [NH=C(NH$_2$)$_2$] or nitroguanidine [NH$_2$C (=NH)NH.NO$_2$].

When X is S, then R$_1$, R$_2$ and R$_3$ are preferably hydrogen. That is the compound thiourea [S=C(NH$_2$)$_2$].

In a preferred embodiment of the invention X is O. R$_3$ is preferably hydrogen. R$_1$ is preferably hydrogen and R$_2$ is preferably hydrogen, hydroxyl, hydrocarbyl, hydroxyhydrocarbyl, carbamyl, 1-acetyl or amino. Alternatively R$_1$ and R$_2$ both may be carbamyl.

Preferably, the hydrocarbyl of R$_1$ and R$_2$ is alkyl, preferably an alkyl with not more than 3 carbon atoms.

Preferably, the hydroxyhydrocarbyl of R$_1$ and R$_2$ is $^-$ROH wherein R is an alkyl.

Preferably the compound of formula I comprises a compound selected from the group consisting of urea [H$_2$NCONH$_2$], hydroxyurea [HONHCONH$_2$], methylurea [CH$_3$NHCONH$_2$], methylolurea [HOCH$_2$NHCONH$_2$], biuret [NH$_2$CONHCONH$_2$], triuret [NH$_2$CONHCONHCONH$_2$], and semicarbazide (or aminourea) [NH$_2$CONHNH$_2$].

Preferably the compound of formula I comprises urea.

The derivative of the adduct may comprise a heterocyclic condensate formed from the adduct where the adduct has an open acid-amide structure or it may comprise a hydrated acid formed from the adduct where the adduct is a heterocyclic condensate.

The polyalk(en)yl succinic anhydride preferably comprises polyisobutenyl succinic anhydride (PIBSA). The PIBSA may have a molecular weight from about 270 to about 2500. Preferably it is from about 950 to about 1200. In one preferred embodiment it is about 1000, and one such product is known in the trade as Lubrizol ADX 101B which has a molecular weight of about 1050.

Preferably the adduct is an adduct of polyalk(en)yl succinic anhydride and urea. Most preferably the adduct is an adduct of PIBSA and urea.

The compound of formula I and the polyalk(en)yl succinic anhydride may be reacted in a molar ratio from 0.5:1 to 1:1; preferably 0.5:1 to 0.75:1; most preferably 0.67:1.

Most preferably it comprises the adduct of urea and PIBSA wherein they have a molar ratio of 0.67:1.

The polyalk(en)yl succinic anhydride and compound of formula I may be reacted with each other at a temperature above 60° C. and preferably below 140° C., prefreably at a temperature from 80 to 120° C., preferably 100 to 120° C., most preferably at 120° C. The reaction time will depend on the reaction temperature and may be from 1 hour (at higher temperatures) to 22 hours (at lower temperatures). Preferably the reaction is carried out at 120° C. for 1 hour.

Without limiting the scope of the invention, it is believed that the adduct which forms when PIBSA reacts with urea is one or more of the following compounds: N-(carbamyl) polyisobutenylsuccinamic acid; its condensate N-(carbamyl)-3-polyisobutenyl-2,5-pyrrolidinedione; N,N'-ketobis(polyisobutenyl-succinamic acid); and its condensate N,N'-ketobis(3-polyisobutenyl-2,5-pyrrolidinedione). It is believed that the preferred adduct which forms is a mixture of the above compounds, and it is believed that the acids form the major portion of such a mixture. It is also believed that if the reaction is carried out a higher temperature for a longer period of time, an increasing amount of the heterocyclic condensates will form.

According to another aspect of the present invention there is provided an emulsifier comprising an adduct or derivative thereof substantially as described hereinabove. Preferably the emulsifier is suitable for use as an emulsifier for water and oil emulsions, preferably as an emulsifier in an emulsion explosive composition. According to another aspect of the present invention there is provided the use of an adduct or derivative thereof substantially as described hereinabove as an emulsifier.

According to another aspect of the present invention there is provided an emulsion including an emulsifier substantially as described hereinabove.

According to another aspect of the present invention there is provided an emulsion comprising a discontinuous liquid phase containing an oxygen supplying component; a continuous liquid phase of an organic medium; and an adduct or derivative thereof substantially as described hereinabove. Preferably the emulsion is an emulsion explosive composition.

The discontinuous phase may comprise an aqueous phase and preferably it comprises an oxidiser salt dissolved in water. The oxidiser salt may comprise a nitrate salt and preferably it comprises ammonium nitrate.

The organic medium may comprise a petroleum product, preferably an oil.

According to yet another aspect of the present invention there is provided an explosive composition comprising a mixture of a dry explosive or oxidising salt; and an emulsion explosive composition substantially as described hereinabove.

According to another aspect of the present invention there is provided a method of preparing a compound comprising reacting polyalk(en)yl succinic anhydride with a compound of formula I.

The compounds may be reacted with each other under heating. Preferably the products are stirred while heated above 60° and preferably below 140° C., preferably at a temperature from 80 to 120° C., preferably 100 to 120° C., most preferably at 120° C. The reaction time will depend on the reaction temperature and may be from 1 hour (at higher temperatures) to 22 hours (at lower temperatures). Preferably the reaction is carried out at 120° C. for 1 hour. Preferably the polyalk(en)yl succinic anhydride is preheated, preferably to about 40° C.

The method may also include the step of forming a heterocyclic condensate of the adduct where the adduct includes an open acid-amide structure. Alternatively it may include the step of forming a hydrated acid of the adduct where the adduct includes a condensated acid.

The compound of formula I and the polyalk(en)yl succinic anhydride may be provided in a molar ratio from 0.5:1 to 1:1, preferably 0.5:1 to 0.75:1, most preferably 0.67:1.

The invention will now be further described by means of the following non-limiting examples.

EXAMPLE 1

Preparation of Adduct

An amount of 317.65 g commercially available PIBSA known as Lubrizol ADX 101B (trade name) was charged into a laboratory reaction vessel.

This was warmed to 40° C. with stirring.

An amount of 7.50 g commercially available fertiliser grade urea (±99% pure) supplied by Kynoch Fertilizers Ltd was added to the reaction flask. Also a diluent in the form of 174.85 g mineral oil BP Enerflex P95 from BP(SA) was added under stirring. The diluent was added to decrease the viscosity.

The reaction flask was heated to 80° C. with continuous stirring for 22 hours at which point examination of small samples from the flask by infra-red absorption spectrometer showed by disappearance of the characteristic absorption peak of the anhydride part of PIBSA, that the latter had reacted essentially completely.

The product was then allowed to cool to room temperature.

EXAMPLE 2

Alternative Preparation of the Adduct

The process of Example 1 was repeated but in this case the reaction flask was heated to 120° C. with continuous stirring for 1 hour, at which point examination of samples again showed that the PIBSA had reacted essentially completely.

EXAMPLE 3

Preparation of Alternative Adduct

An amount of 317.65 g commercially available PIBSA known as Lubrizol ADX 101B (trade name) was charged into a laboratory reaction vessel.

This was warmed to 40° C. with stirring.

An amount of 9.50 g commercially available thiourea (±99% pure) was added to the reaction flask. Also a diluent in the form of 174.85 g mineral oil BP Enerflex P95 from BP(SA) was added under stirring. The diluent was added to decrease the viscosity.

The reaction flask was heated to 130° C. with continuous stirring for 5 hours at which point examination of small samples from the flask by infra-red absorption spectrometer showed by disappearance of the characteristic absorption peak of the anhydride part of PIBSA, that the latter had reacted essentially completely.

The product was then allowed to cool to room temperature.

EXAMPLE 4

Preparation of Base Emlusion Composition

A lipid phase was prepared by diluting 105.0 g of the reaction product of, in turn, example 1, example 2 or example 3 with 195.0 g of a commercially available high flash point petroleum solvent known as Shellsol 2325 (trade name).

An amount of 82.25 g of this lipid phase was mixed with 1000.0 g of a hot (80° C.) aqueous ammonium nitrate solution (having a crystallising temperature of 65° C.) under high shear conditions in a Silverson mixer until an invert emulsion was formed. The aqueous ammonium nitrate solution comprised 82% by mass ammonium nitrate. This emulsion, while still hot, was pumped through an orifice-type homogeniser to reduce the droplet size and attain a viscosity at 70° C. of about 20,000 mNs/m$^2$ (20,000 centipoise).

The emulsion was allowed to cool to room temperature.

EXAMPLE 5

Preparation of Bulk Emulsion Explosive Composition

Each base emulsion of example 4 (in an amount of 100.0 g) was mixed with 65.7 g of commercially available ammonium nitrate (known as Porous Prill Ammonium Nitrate (trade name)) supplied by African Explosives Limited. In this way three samples of a typical bulk explosive formulation were formed.

The two bulk emulsion explosive compositions derived from examples 1 and 2 were stored at ambient temperature, exposed to room air and examined weekly for a period of three months. Even after three months, these compositions were judged to have crytallised to a lesser extent than control samples made with a PIBSA/monoethanol amine emulsifier.

The bulk emulsion explosive composition derived from example 3 was stored at ambient temperature, exposed to room air, for a period of one week, and was judged to have retained its initial appearance and quality for that period. This was sufficient to indicate that the adduct of example 3 was capable of forming a commercially useful emulsion explosive composition, as such completely formulated compositions, in bulk explosives applications, are seldom required to undergo a delay of longer than a week before being detonated.

EXAMPLE 6

Using the adduct of example 2, emulsions were prepared as set out in example 4. However in this case the amount of adduct was selected to provide four emulsions respectively containing 1.06; 0.91; 0.76 and 0.61 percent of the adduct on a mass/mass basis. Emulsion explosives were prepared as set out in example 5 but utilising the above emulsions. In each case the emulsion explosive comprised 6 parts emulsion composition to 4 parts porous prilled ammonium nitrate (parts calculated on a mass basis).

Emulsion explosives containing a conventional emulsifier in the form of the adduct of PIBSA and monoethanolamine were also prepared. The adduct was prepared by reacting PIBSA and the monoethanolamine in a molar ratio of 1:1 and the product was uncondensed. Using this adduct, emulsions with concentrations as set out in the previous paragraph were prepared, and the emulsion explosives were prepared in the same way as set out above.

The emulsion explosives were considered on a weekly basis for their storage quality. The rating scale for the storage quality is as follows:

0 No visible crystallisation at all (best possible result)
1 Trace or very slight crystallisation
2 Partial crystallisation
3 Heavily crystallised
4 Completely crystallised (hard) (worst possible result)

The results are reflected in Table 1

TABLE 1

| | STORAGE QUALITY | | | | | | |
|---|---|---|---|---|---|---|---|
| Emulsifier Used in emulsion explosive | Emulsifier dosage in emulsion, actual active polymeric surfactant, % mass/mass | Sample age, weeks | | | | | |
| | | 1 | 2 | 3 | 4 | 5 | 6 |
| Adduct of Example 2 | 1.06 | 0 | 0 | 0 | 0 | 0 | 1 |
| | 0.91 | 0 | 0 | 0 | 0 | 1 | 1 |
| | 0.76 | 0 | 0 | 0 | 0 | 1 | 1 |
| | 0.61 | 0 | 0 | 0 | 0 | 1 | 2 |
| Conventional Emulsifier | 1.06 | 0 | 0 | 0 | 1 | 2 | 3 |
| | 0.91 | 0 | 0 | 2 | 3 | 4 | 4 |
| | 0.76 | 0 | 0 | 2 | 3 | 4 | 4 |
| | 0.61 | 0 | 0 | 2 | 3 | 4 | 4 |

The superior emulsion properties of the product of the present invention over a conventional emulsifier is clearly demonstrated.

Further, the product of at least example 2 made a useful doped emulsion explosive with a six-week useable shelf life at only 0.31% by mass active emulsifier in the emulsion, and a stable invert type explosives emulsion could still be made at only 0.15% by mass active emulsifier in the emulsion. Present commercially used emulsifiers for emulsion explosives are quite incapable of such performance since they need higher concentrations of the emulsifier.

It was also found that adducts of at least example 2 improved the ease with which an emulsion could be formed.

Furthermore it is known that explosive emulsifiers in which the PIBSA/monoethanolamine headgroup is of the uncondensed (amide/acid) type, are known to be capable of interacting chemically with (excess) sodium nitrite in chemically gassed emulsion. Under unfavourable circumstances, emulsion break-up can occur as a result, causing gross crystallisation of oxidiser salts and total emulsion quality failure sometimes within hours of manufacture. Aggravating conditions for failure are: low emulsifier dosage in the emulsion, poor refinement (large droplet size) and high unreacted nitrite levels (which can sometimes occur in commercial emulsion explosives products). Initial tests showed that the use of the adduct of example 2 showed itself less prone than the conventional emulsifiers (adduct of PIBSA/monoethanolamine) to cause an emulsion quality problem by interaction with excess nitrite in the emulsion.

It will be appreciated that many variations in detail are possible without thereby departing from the scope and spirit of the invention.

What is claimed is:

1. An adduct of polyalk(en)yl succinic anhydride and a compound of formula I:

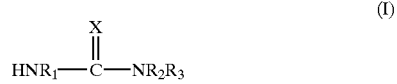

wherein
R$_1$ is hydrogen, hydroxyl, hydrocarbyl, hydroxyhydrocarbyl, carbamyl, 1-acetyl, amino, or nitro;
R$_2$ is hydrogen, hydroxyl, hydrocarbyl, hydroxyhydrocarbyl, carbamyl, 1-acetyl, amino, or nitro;
R$_3$ is hydrogen or hydrocarbyl; and X is O, S, or NH;

or a derivative of such an adduct.

2. The adduct or derivative thereof of claim 1 wherein the compound of formula I is guanidine or nitroguanidine.

3. The adduct or derivative thereof of claim 1 wherein the compound of formula I is thiourea.

4. The adduct or derivative thereof of claim 1 wherein X in formula I is O.

5. The adduct or derivative thereof of claim 4 wherein the compound of formula I is selected from the group consisting of urea ($H_2NCONH_2$), hydroxyurea ($HONHCONH_2$), methylurea ($CH_3NHCONH_2$), methylolurea ($HOCH_2NHCONH_2$), biuret ($NH_2CONHCONH_2$), triuret ($NH_2CONHCONHCONH_2$), and semicarbazide (aminourea or $NH_2CONHNH_2$).

6. The adduct or derivative thereof of claim 5 wherein the compound of formula I is urea.

7. The adduct or derivative thereof of any one of claims 1–5 wherein the polyalk(en)yl succinic anhydride is polyisobutenyl succinic anhydride (PIBSA).

8. The adduct or derivative thereof of claim 7 wherein the PIBSA has a molecular weight from about 950 to about 1200.

9. The adduct or derivative thereof of claim 1 wherein the polyalk(en)yl succinic anhydride is PIBSA and the compound of formula I is urea.

10. The adduct or derivative thereof of claim 1 wherein the compound of formula I and the polyalk(en)yl succininic anhydride are reacted in a molar ratio from 0.5:1 to 1:1.

11. An emulsifier comprising an adduct or derivative thereof of claim 1.

12. The emulsifier of claim 11 which is an emulsifier for water and oil emulsion explosive compositions.

13. An emulsion comprising an emulsifier of claims 11 or 12.

14. An emulsion comprising a discontinuous liquid phase containing an oxygen supplying component; a continuous liquid phase of an organic medium; and an emulsifier of claims 11 or 12.

15. The emulsion of claim 14 wherein the discontinuous phase comprises an aqueous phase in the form of an oxidiser salt dissolved in water.

16. The emulsion of claim 15 wherein the organic medium comprises an oil.

17. An explosive composition comprising a mixture of a dry explosive or oxidising salt; and an emulsion of claim 16.

18. A method for emulsifying a mixture of at least two immiscible liquids comprising mixing the immiscible liquids with an adduct or a derivative of claim 1.

19. The method of claim 18 wherein a first liquid phase contains an oxygen supplying component; and a second liquid phase is an organic medium.

20. The method of claim 19 wherein the first liquid phase comprises an aqueous phase of an oxidiser salt dissolved in water.

21. The method of claim 19 wherein the organic medium comprises an oil.

22. A method of preparing a compound comprising reacting polyalk(en)yl succinic anhydride with a compound of formula I:

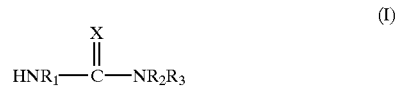

(I)

wherein $R_1$ is hydrogen, hydroxyl, hydrocarbyl, hydroxyhydrocarbyl, carbamyl, 1-acetyl, amino, or nitro;

$R_2$ is hydrogen, hydroxyl, hydrocarbyl, hydroxyhydrocarbyl, carbamyl, 1-acetyl, amino, or nitro;

$R_3$ is hydrogen or hydrocarbyl; and

X is O, S, or NH.

* * * * *